United States Patent [19]

Coulter

[11] Patent Number: 5,704,360
[45] Date of Patent: Jan. 6, 1998

[54] ULTRASOUND BONE ANALYZERS AND METHODS FOR SENSING BODY PART

[75] Inventor: George Gary Coulter, Chard, England

[73] Assignee: Lilly Industries Limited, Basingstoke, England

[21] Appl. No.: 704,204

[22] Filed: Aug. 28, 1996

[30] Foreign Application Priority Data

Aug. 30, 1995 [GB] United Kingdom ............ 9517697

[51] Int. Cl.[6] ........................................... A61B 8/00
[52] U.S. Cl. ........................................... 128/661.03
[58] Field of Search ............... 128/660.01, 660.04, 128/660.07, 660.08, 661.03, 779; 73/172

[56] References Cited

U.S. PATENT DOCUMENTS 5,010,774  4/1991  Fikuo et al. ............... 73/862.04
5,396,891  3/1995  Whitney et al. ........... 128/661.03

Primary Examiner—Francis Jaworski
Attorney, Agent, or Firm—Michael T. Bates; David E. Boone

[57] ABSTRACT

The position of a bone in a body part e.g. a heel 15 is sensed by placing the foot 13 on a surface 12 and sensing pressure points between the underface 14 of the foot and the surface 12. The surface 12 is part of a xerographic device. The distances between pressure points are compared with stored data to obtain for example a measurement of bone condition using ultrasound transducers 19. The body part could be a hand (FIG. 1).

4 Claims, 3 Drawing Sheets

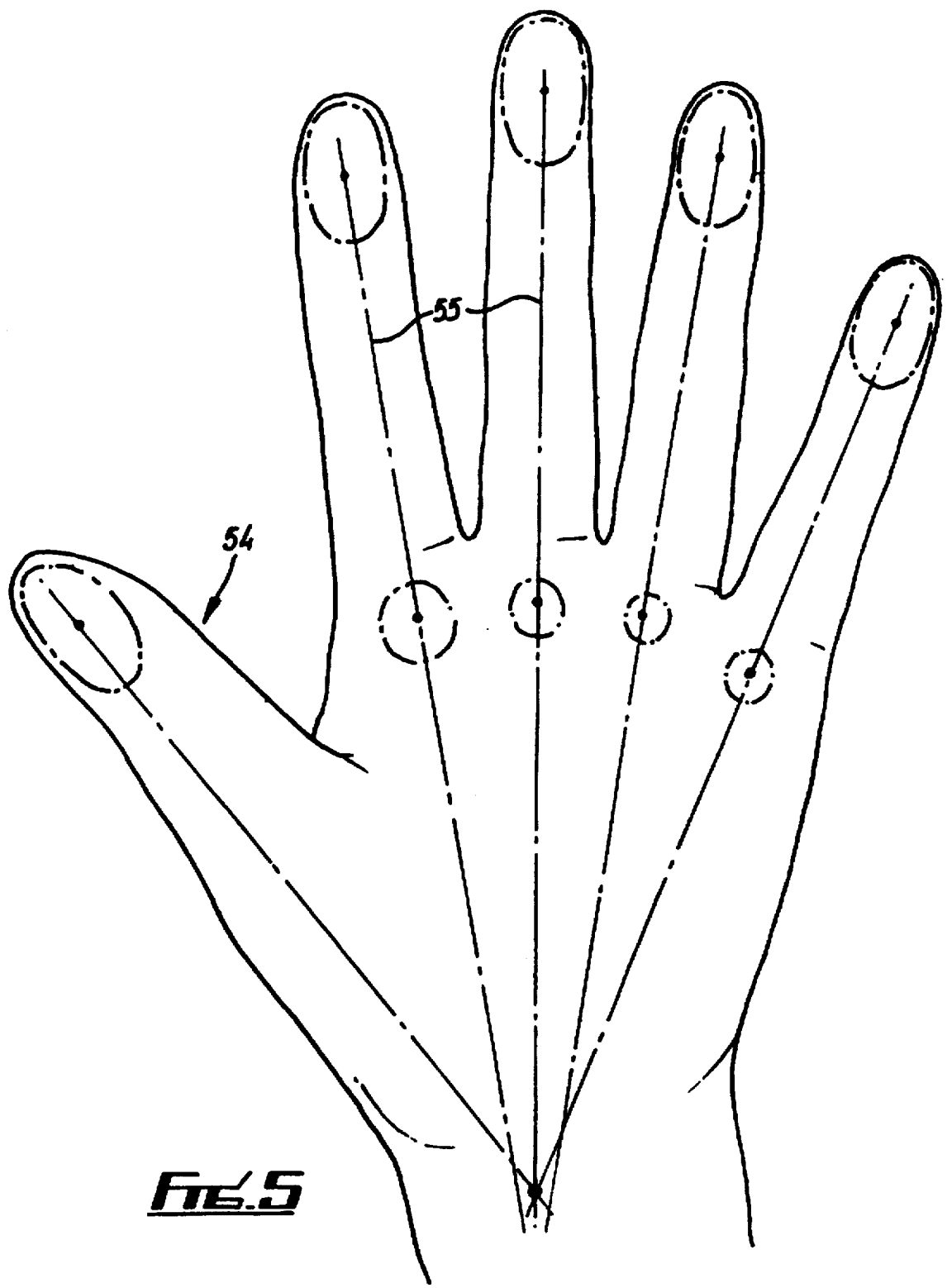

ULTRASOUND BONE ANALYZERS AND METHODS FOR SENSING BODY PART

This invention relates to ultrasound bone analysers and methods for sensing body parts.

The assessment of bone condition using ultrasound is well-known. Examples of devices and methods are described in EP-A-0576217 and GB-A-2257253.

Such assessment is useful in detecting or monitoring the risk of bone fracture which can arise because of osteoporosis.

A disadvantage of existing devices is that the positioning of a bone is not easily reproducible, thus making difficult the accurate monitoring of bone condition over a period of time.

One form of use is in relation to a calcaneal (heel) measure of bone condition.

It is desirable for accurate assessment that repeat measurements should measure the same part of the bone as nearly as possible, and the present invention is directed towards achieving this.

According to one aspect of the invention an ultrasound bone analyser apparatus comprises means for locating a patient's body part, ultrasound means for assessing the condition of bone in the body part and means for effecting relative movement between the ultrasound means and the body part characterised in that xerographic means are provided for sensing the position of the body part.

There may be means responsive to the xerographic sensing means for effecting the relative movement.

The ultrasound means may be moved to obtain the relative movement.

In some cases the ultrasound means comprises two transducers, only one transducer being moved.

The xerographic means may comprise a surface against which a surface of the body part can be pressed.

From another aspect the invention provides a method of using an ultrasound bone analyser apparatus comprising positioning a body part in relation to ultrasound means, sensing the position of the body part, and adjusting the position of the ultrasound means in relation to the body part in response to the sensed position.

The invention also provides a method of locating a body part for diagnostic testing comprising locating the body part on a surface and sensing points of pressure between the body part and the surface.

The invention may be performed in various ways and one specific embodiment with possible modifications will now be described by way of example with reference to the accompanying diagrammatic drawings, in which:

FIG. 5 is another print;

Figure 1:
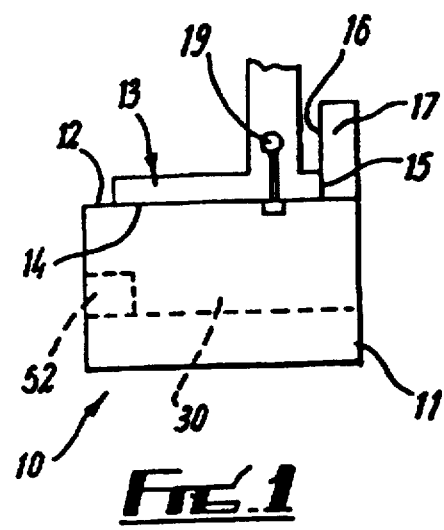
FIG. 1 is a side view of ultrasonic bone analyser apparatus.
Figure 2:
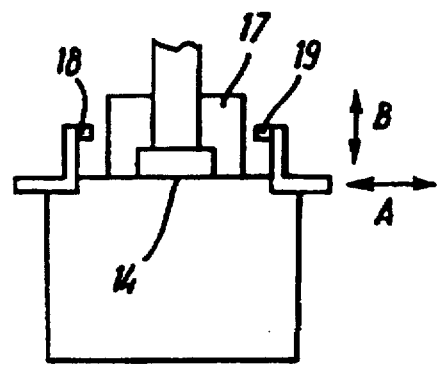
FIG. 2 is a front view of FIG. 1.

Referring to FIGS. 1 and 2, ultrasound bone analyser apparatus 10 comprises a housing 11 providing a flat surface 12 on which a patient's foot 13 can rest with the underface 14 of the foot 13 engaging the surface 12 and the back of the heel 15 just engaging the front surface 16 of an upright portion 17.

In assessing bone condition, it is desirable to take several measurements over a period of time, and the measurements may be separated by, for example, two months. It is important for the usefulness of the assessments that the measurements be taken of the same part of bone because if there is a difference in orientation of the body part relative to the ultrasound means between measurements, this can lead to inconsistency reducing their usefulness in assessing bone condition or change in bone condition.

In the present case, before making a measurement, the position of the body part is sensed and the ultrasound transducers are positioned in response to the sensed position of the body part.

Ultrasound transducers 18, 19 are mounted on opposite sides of the heel 15 and are connected to means 20 for adjusting the position of the respective transducers 18, 19 towards and away from the heel 15 (arrow A) and up and down (arrow B).

Figure 3:
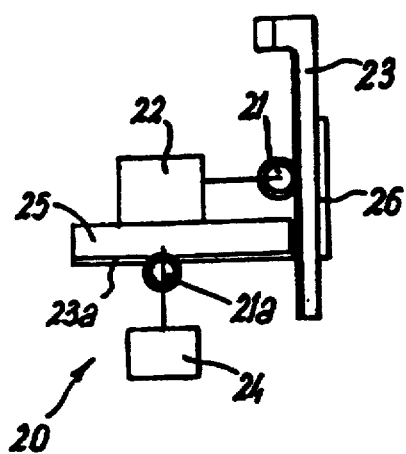
FIG. 3 shows drive means.
Figure 6:
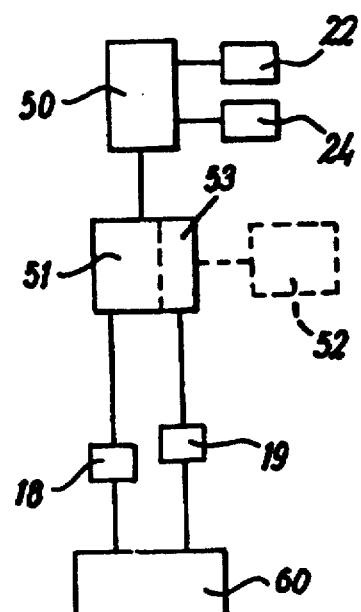
FIG. 6 shows a control arrangement.

The means 20 could for example be a gear 21 driven by an electric motor 22, the gear engaging and moving a rack 23 connected to the transducer (FIG. 3) and a second electric motor 24 for driving a gear 21a engaging rack 23a on support 25 for moving a support 25, 26 for the motor 22 and rack 23, the rack 23 sliding up and down on support 26.

Various means can be used for sensing the position of the body part.

In the arrangement of FIGS. 1 and 2 the apparatus includes a xerographic device 30 in housing 11 and the surface 12 is a glass sheet forming part of the xerographic device 30.

Figure 4:
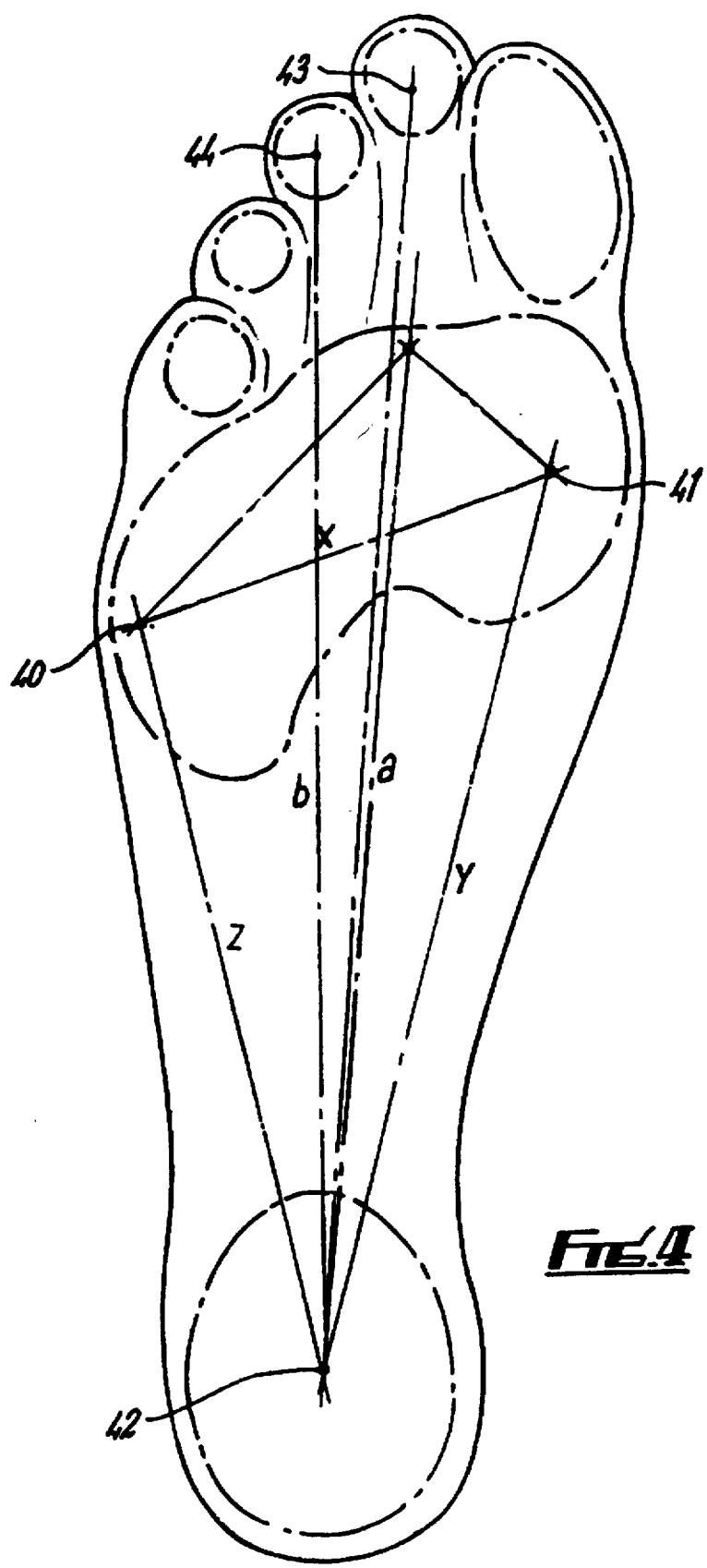
FIG. 4 is a xerographic print.

FIG. 4 shows an example of a xerographic print of the underface 14 of a foot and the three points 40, 41, 42 indicate where the underface 14 of the foot produces the highest pressure on surface 12.

The three distances x, y, z between the points 40 and 41, 41 and 42, 42 and 40 are related to the height of a particular part of the heel above the surface 12, and also to the position of the heel part horizontally in relation to a vertical plane.

A large number of such relationships are obtained by accurately measuring a corresponding number of individuals to provide a data store of such relationships.

The particular distances x, y, z for a given measurement are then compared with those in the data store and the height and lateral position of the body part (bone) to be measured is obtained.

The position of one or both transducers 18, 19 is then adjusted accordingly. This can be done by manual control of motors 22, 24, or the position data can be input to a control 50 for the motors. The input can be manual or electrical if the data store is in a computer 51.

The relative positions of the bone and the transducers can thus be reproduced, and the part of the bone being measured is thus essentially the same for each of the various measurements.

The foot should not move during the position sensing and bone measurement.

In one example a xerographic print is not produced, but the positions of points 40, 41, 42 are noted by sensors 52 in housing 12 responsive to electric charge which are connected to computer 51 to input the distances x, y, z to a comparator 53 in the computer to produce the transducer position control signals for appropriately positioning the transducers. The points 40, 41, 42 correspond to highest pressure and darkest points if a print were made.

In one arrangement a latent image of the foot on surface 12 is stored in the computer and can be compared with stored data; the image could be stored and compared with a similar image at the next occasion of measurement to bring the images into correspondence prior to measurement.

If the measurement is largely done by hand, a normal xerographic print can be obtained on paper carrying grid markings and the grid positions x, y, z can be read off and keyed into a control apparatus for the transducers.

In another arrangement, the surface 12 is provided by or with a large number of pressure sensors which provide output signals to the comparator which responds to the signals of highest pressure at points 40, 41, 42 to produce control signals for the positioning of the transducers.

It is possible for another bone part of the body to be measured, for example as in FIG. 5 a hand 54 may be pressed against surface 12 producing lines 55 between maximum pressure points associated with the fingers and these can be correlated with corresponding stored data. In this case the position of the distal radius may be determined.

The transducers 18, 19 may be such that one transmits and one receives or both may selectively transmit and receive.

The transducers 18, 19 are controlled by unit 60 in known manner to effect the measurement and obtain details of bone condition; the procedure is known to the skilled person; examples are in EP-A-0576217 and GB-A-2257253.

The invention can also be applied in to the study of bone condition in animals.

I claim:

1. An ultrasound bone analyser apparatus comprising a housing having a surface on which a patient's body part can rest, ultrasound means mounted on the housing for assessing the condition of bone in the body part, means mounted on the housing for effecting relative movement between the ultrasound means and the body part and xerographic means associated with the housing surface for sensing the position of the body part, said xerorgraphic means being coupled to means responsive to the xerorgraphic sensing means for effecting said relative movement.

2. The apparatus as claimed in claim 1 wherein the ultrasound means is movable to obtain the relative movement.

3. The apparatus as claimed in claim 2, wherein the xerographic means comprises a xerographic surface plate configured to receive a surface of the body part.

4. A method of using an ultrasound bone analyser apparatus comprising: positioning a body part having bone therein in relation to an ultrasound means coupled to the apparatus, sensing the position of the body part using a xerographic device, and adjusting the position of the ultrasound means in relation to the body part in response to the sensed position.

* * * * *